United States Patent [19]
Kanert et al.

[11] Patent Number: 5,190,553
[45] Date of Patent: Mar. 2, 1993

[54] METHOD AND APPARATUS FOR FOLDING A RESILIENT INTRAOCULAR LENS

[75] Inventors: Otmar Kanert; Jochen Kammann; Ulrich Dretzler, all of Dortmund, Fed. Rep. of Germany

[73] Assignee: adatomed Pharmazeutische und medizintechnische Gesellschaft mbH, Munich, Fed. Rep. of Germany

[21] Appl. No.: 831,841

[22] Filed: Feb. 6, 1992

[30] Foreign Application Priority Data

Mar. 14, 1991 [DE] Fed. Rep. of Germany ....... 4108303

[51] Int. Cl.⁵ .................. A61B 17/00; A61F 9/00; A61F 2/16
[52] U.S. Cl. .......................................... 606/107; 623/6
[58] Field of Search ............................ 606/107; 623/6

[56] References Cited

U.S. PATENT DOCUMENTS 4,919,130 4/1990 Stoy et al. .......................... 606/107

FOREIGN PATENT DOCUMENTS 3348066 8/1983 Fed. Rep. of Germany .

Primary Examiner—Ronald Frinks
Attorney, Agent, or Firm—Keck, Mahin & Cate

[57] ABSTRACT

In a method and apparatus for folding a resilient intraocular lens, the lens is fixed on a support surface and then folded by means of two pressing members which are moved synchronously towards each other in such a way that the intraocular lens conforms on a slightly reduced scale to the interior of a tube member of a lens implantation instrument. The lens is then released from its support surface and pressed into the interior of the implantation instrument tube member.

5 Claims, 3 Drawing Sheets

METHOD AND APPARATUS FOR FOLDING A RESILIENT INTRAOCULAR LENS

BACKGROUND OF THE INVENTION

The invention concerns a method and an apparatus for folding a resilient intraocular lens.

When a cataract operation is performed, an intraocular lens comprising a resilient material such as more particularly silicone is inserted in a folded condition into the natural eye capsule which has remained in the eye. In that respect the operation of putting the intraocular lens into a folded condition is often a really troublesome procedure as, during the folding operation the resilience of the lens means that the lens frequently jumps out from between the two gripping elements of the implantation instrument which is normally in the form of a tweezer-like instrument. That occurs whenever the resilient lens body is not exactly positioned between the gripping elements of the implantation instrument.

More specifically, various forms of a surgical device for the implantation of deformable intraocular lenses are to be found in German patent specification No. 3 348 066. In one embodiment of such a device, two elongate jaws which are movable in opposite relationship to each other co-operate to form a closed cavity which serves to receive the compressed or folded intraocular lens. With that device, the intraocular lens is clamped in widely varying forms between the elongate jaws, with the lens being disposed therebetween in a somewhat random fashion. It is not possible to exclude the possibility of damage occurring when the intraocular lenses are handled in that way. In addition problems occur upon operative intervention in the eye as the lens comes out of the device in a relatively uncontrolled fashion, depending on the way on which it was randomly disposed between the two jaws. Furthermore, the fact that the lens has to be manually introduced into the device means that the medical personnel carrying out that operation have to meet relatively high demands in terms of their skill in carrying out that operation.

Another device described in the above-indicated patent specification has a chamber for receiving the undeformed intraocular lens, and the intraocular lens can be pressed into the eye by means of a pressure agent through an outlet opening of very small cross-section. With that device the lens is also pressed through the outlet opening in an arbitrary fashion for, depending on the way in which the lens comes to lie in front of the outlet opening in a random configuration, it will tend to be folded together in an undefined fashion. It will be appreciated that that means that the lens cannot issue from the instrument and pass into the eye in a defined uniform fashion. Damage to the sensitive intraocular lens when it is being pressed through the narrow outlet opening is also a possibility which cannot be excluded.

SUMMARY OF THE INVENTION

An object of the present invention is to provide a method of folding a resilient intraocular lens which provides a defined and regular folding action.

Another object of the present invention is to provide a method of folding a resilient intraocular lens using mechanical means which nonetheless ensures that the lens is handled in a careful fashion and is folded in a specifically defined manner so that it can be exactly positioned in a lens implantation instrument.

Still another object of the present invention is to provide a method of folding a resilient intraocular lens which affords controlled folding of the lens in a positive and careful fashion.

A still further object of the present invention is to provide an apparatus for folding an intraocular lens using mechanical means which provides for defined controlled and careful folding of the lens for precise positioning in an implantation instrument.

In accordance with the principles of the present invention the foregoing and other objects are achieved by a method of folding a resilient intraocular lens in which the lens is first fixed on a support surface, for example mechanically or by other means such as pneumatically or by virtue of a suction effect. The lens is then folded by means of first and second feed pressing members which are movable synchronously in opposite relationship to each other and which move towards the intraocular lens to produce folding thereof in such a way that the lens reproduces or simulates in a slightly reduced configuration the internal contour of a tube member of an implantation instrument. After release of the fixing effect the folded lens is pressed into the interior of the tube member of the implantation instrument.

In another aspect, the foregoing and other objects are achieved by an apparatus for folding a resilient intraocular lens, for carrying out the method of the invention, comprising first and second feed pressing members which are synchronously movable in mutually opposite relationship, and a support surface for supporting the intraocular lens. When the feed pressing members are in the condition of being brought together, at their sides which are in contact with the intraocular lens, they simulate or reproduce in a slightly reduced fashion the internal contour of a tube member of an implantation instrument. The apparatus further includes a lens fixing means for holding the intraocular lens on the support surface and an insertion pressing member adapted to move in the direction of the interior of the tube member of the implantation instrument, to move the lens in a folded condition into the tube member.

As will be seen in greater detail hereinafter with reference to a preferred embodiment of the apparatus according to the invention, the feed pressing members have end faces which face towards and are adapted to co-operate with the intraocular lens, being of a concavely rounded configuration so that their shape approximately corresponds to the internal contour of the tube member of the implantation instrument. Prior to the folding operation being effected, the tube member is secured to the folding apparatus by a suitable clamping device, with the tube member being disposed in orthogonal relationship to the movement of the two feed pressing members. The configuration of the end faces of the feed pressing members which move towards each other and thus towards the intraocular lens to be folded causes the haptic of the intraocular lens to move along the concave configurations of the end faces of the feed pressing members, thus beginning the operation of folding the intraocular lens on to itself. In the final position of the feed pressing members, that is to say when the lens folding operation is concluded, the lens support surface and the end faces of the feed pressing members reproduce the internal contour of the tube member, on a slightly smaller scale, so that the intraocular lens which is now in a folded condition can be pushed into the interior of the tube member of the implantation instrument, by means of an insertion member, in a direction which is perpendicular to the folded cross-section of the lens.

In a preferred feature of the invention the support surface of the apparatus is recessed in a conical configuration in the region on which the optical part of the intraocular lens is supported, with the depth of the conical recess being for example about 0.3 mm. That improves positioning of the lens, in conjunction with the fixing means. The fixing means can be a mechanical fixing means in the form of a hold-down means for holding the intraocular lens down against the fixing surface, the hold-down means being movable towards the support surface to hold the lens thereagainst. The hold-down means prevents the optical part of the lens from lifting when the feed pressing members move towards each other to engage the lens. It is also possible however to use pneumatic fixing means with which the intraocular lens is held against the lens support surface by a slight suction effect. Prior to the folded intraocular lens being inserted into the interior of the tube member of the implantation instrument, the operative effect of the fixing means is removed by withdrawal of the mechanical hold-down means or by switching off the suction effect.

Preferably, a mechanical abutment means is provided for limiting the movement of a mechanical hold-down means so that the hold-down means is stopped in a position in which it bears against the optical part of the intracular lens practically without applying a force thereto. The abutment means is preferably adjustable in dependence on the thickness of the respective lens being folded. As indicated the function of the hold-down means is to prevent the optical part of the lens from lifting off the support surface in the folding operation.

Depending on the shape of the internal contour of the tube member of the implantation instrument, the final shape of the intraocular lens in the folded condition may be from round to that of a flat ellipse.

The folding operation in the method according to the invention ensures that the intraocular lens is handled in an extremely careful fashion as bending of the resilient material thereof occurs for the major part in the non-optical portion of the lens and the transitional radii forming the bent configuration of the lens in the folded condition are relatively generous.

Preferably, the folding apparatus according to the invention is used when inserting a folded intraocular lens into an implantation instrument as is described in pending U.S. patent application Ser. No. 07/727,938, filed Jul. 10, 1991 to which reference is hereby directed as incorporation thereof.

The use of a sterile liquid which provides for a better sliding movement of the lens in the folding operation and when it is inserted into the interior of the tube member of the implantation instrument is desirable.

The method according to the invention and the apparatus according to the invention for carrying out the method can be used for folding many different intraocular lenses into a defined shape. As a result it is possible for the lenses always to be adapted to the cross-sectional size and configuration of the interior of the tube member of the implantation tool, into which they are to be inserted. That uniformity of folding and insertion ensures that the intraocular lens always exhibits the same unfolding behaviour and characteristics when being inserted into the eye in the course of surgical intervention.

Further objects, features and advantages of the present invention will be apparent from the following description of a preferred embodiment.

DESCRIPTION OF THE PREFERRED EMBODIMENT

Figure 1:
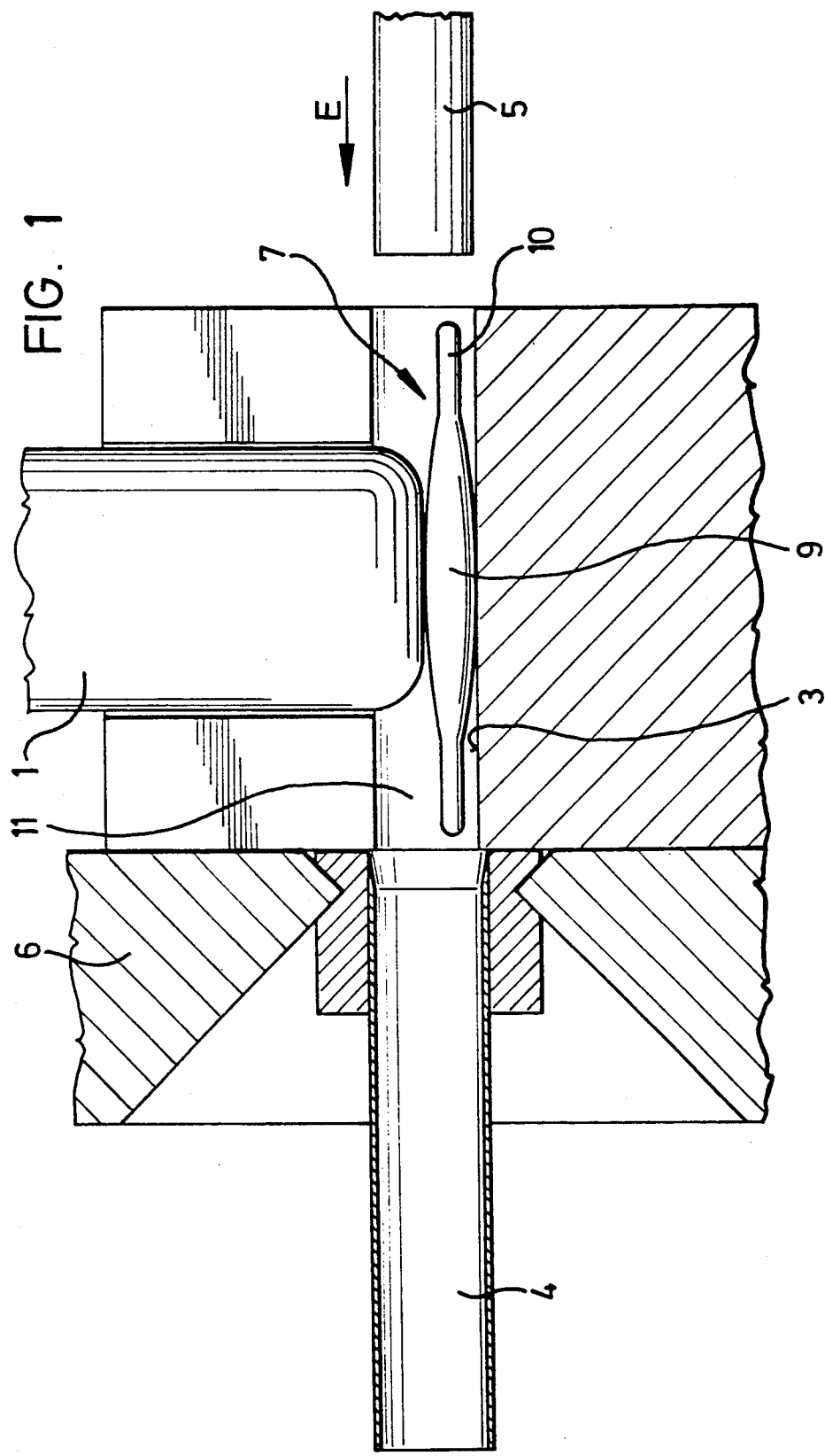
FIG. 1 is a side view of a part of a preferred embodiment of an apparatus according to the invention, with an inserted intraocular lens in a non-folded condition therein.
Figure 2:
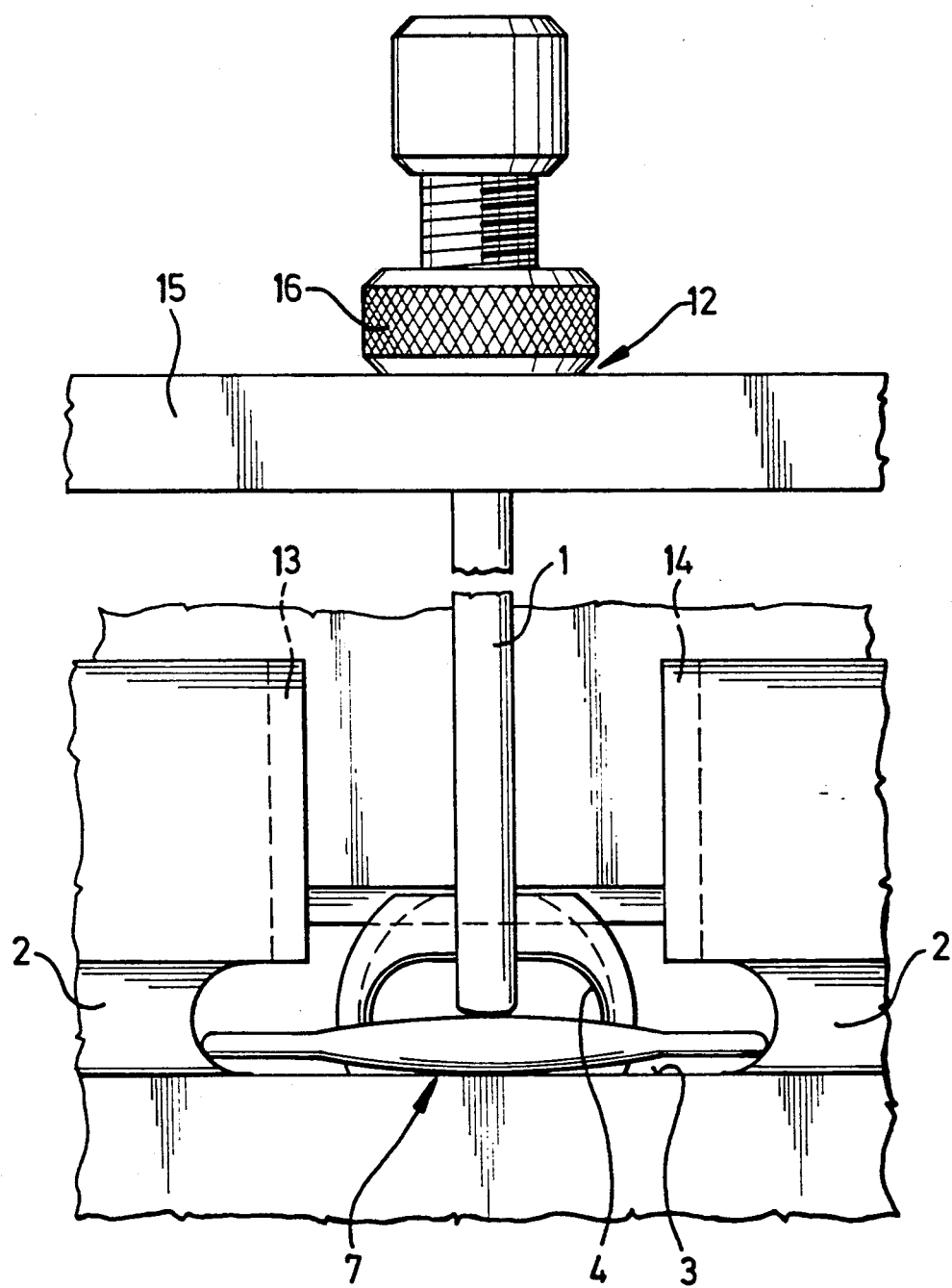
FIG. 2 is a front view of the part of the structure shown in FIG. 1.

Referring firstly to FIGS. 1 and 2, shown therein is a part of an apparatus for carrying out a method according to the invention for folding a resilient intraocular lens. Reference numeral 3 in FIGS. 1 and 2 shows a support means having a support surface for supporting an intraocular lens which is indicated at 7. After the intraocular lens 7 has been fitted into position in the apparatus, resting on the support surface of the support member 3, a lens fixing member in the form of a hold-down member diagrammatically indicated at 1 is moved downwardly until it is stopped in its downward movement by reaching a mechanical abutment indicated at 12 in FIG. 2. When the hold-down member 1 is in that position, it lies on the optical part of the lens which is indicated at 9 in FIG. 1, practically without applying a force thereto. When the lens is held in that position, first and second feed pressing members which are shown at reference 2 in FIG. 2 and which are movable synchronously in opposite relationship to each other then move towards each other and thus towards the lens 7 which is disposed therebetween. It will be seen from FIG. 2 that the end faces of the feed pressing members 2 which face towards the intraocular lens 7 are of a concavely rounded configuration so that their shape approximately corresponds to the inside contour of a tube member as indicated at 4 in FIG. 1 of an implantation instrument. It will be noted at this point that the tube member 4 is fixed to the lens folding apparatus by a clamping device indicated at 6 in FIG. 1, prior to the lens folding operation beginning. The tube member 4 is disposed in orthogonal relationship to the feed movement of the feed pressing members 2. When the end faces of the feed pressing members 2 come into contact with the haptic as indicated at 10 of the intraocular lens 7, the rounded configuration of the end faces of the feed pressing members 2 means that the haptic is bent or curved thereagainst and moves along the concavely rounded end faces, so that the lens folding operation then begins. The hold-down member 1 prevents the optical part of the lens 9 from lifting off the support surface 3, during the folding operation.

Figure 3:
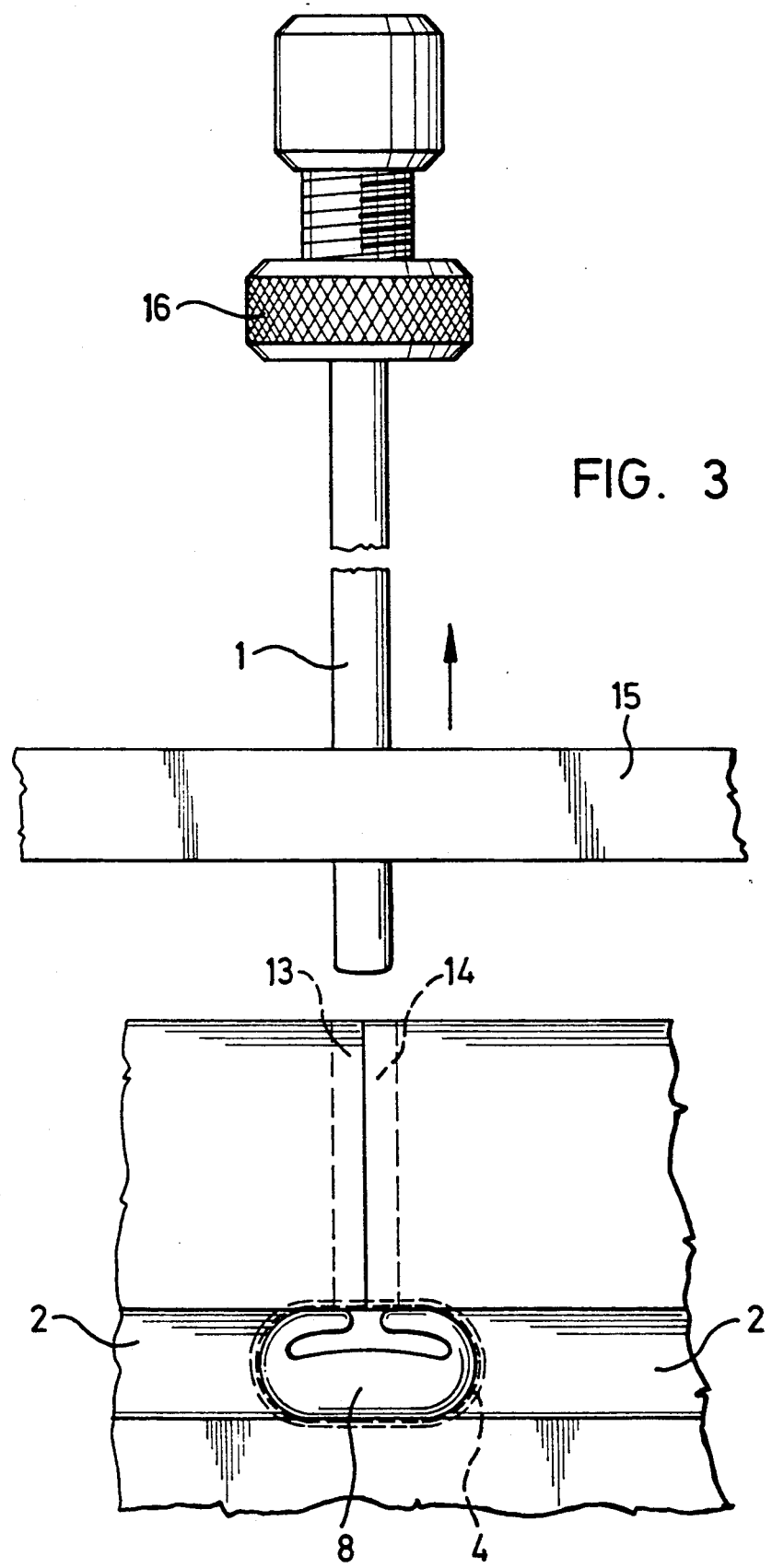
FIG. 3 shows the same view as that shown in FIG. 2, after the folding operation has been concluded.

After termination of the movement of the feed pressing members 2 towards each other, the end faces thereof and the support surface 3 co-operate to define a contour which corresponds to the contour of the interior of the tube member 4 of the implantation instrument, while however being slightly smaller than same, as shown by the broken-line view in FIG. 3 wherein the broken line indicates the configuration of the tube member 4 of the implantation instrument. In this embodiment the internal contour of the tube member 4 is of an oval shape but it is also possible to use an approximately circular contour.

Looking now at FIGS. 2 and 3 the feed pressing members 2 have recesses 13 and 14 which are matched to the cross-section of the hold-down member 1. For the purposes of effecting the lens folding operation, it is advantageous for the cross-section of the hold-down member 1 to be elongate, more specifically being elongate in the direction indicated at E in FIG. 1 in which the folded lens is to be inserted into the tube member 4 of the implantation instrument, that is to say, elongate perpendicularly to the folding direction visible in FIGS. 2 and 3.

After termination of the lens folding operation, an insertion pressing member 5 whose direction of movement is in orthogonal relationship to the movement of the feed pressing members 2 is moved towards the folded intraocular lens as indicated at 8 in FIG. 3, and the folded lens is thus inserted into the interior of the tube member 4 of the implantation tool. It will be seen therefore that the lens is inserted into the tube member 3 in a direction which is perpendicular to its folded cross-section.

As noted above, prior to the beginning of the lens folding operation, the tube member 4 of the implantation instrument is secured to the lens folding apparatus by the clamping device 6 in such a way that the internal contour of the tube member 4 is aligned with an ejection passage formed by the co-operation of the rounded end faces of the two feed pressing members 2. In that way the folded lens 8 can be pushed into the interior of the tube member 4 of the implantation instrument by the insertion pressing member 5, without the lens suffering damage in that operation. Therefore, the lenses 8 which are always folded in a uniform fashion by operation of the above-described apparatus are always positioned in the same defined position in the tube member 4 of the implantation tool.

The above-described apparatus can be further improved in a simple fashion by the support surface 3 for supporting the optical part of the lens 9 having a conical recess of a depth of for example about 0.3 mm. In that way the lens can be positioned in a better defined fashion. Furthermore, the recess, in conjunction with the hold-down member 1, can provide that the haptic 10 of the lens is lifted slightly away from the support surface 3, thus providing an improved preliminary bent configuration to enable the actual lens folding procedure to be initiated more readily. The same effect can also be achieved when using a lens fixing device which operates on the basis of a suction effect for holding the lens against the support surface 3.

So that the hold-down member 1 bears as far as possible practically without applying a force against the intraocular lens to be folded, the hold-down member 1 comes to bear against an abutment 12 when the hold-down member 1 is in its position of being applied to the intraocular lens. In the illustrated embodiment, as shown in FIGS. 2 and 3, the abutment 12 is formed by a screw nut 16 which can be displaced on the hold-down member 1. The screw nut 16 co-operates with a main plate member 15 of the folding apparatus, thereby to form the abutment as indicated at 12, as shown in FIG. 2. The screw nut 16 is adjusted on the hold-down member 1, depending on the thickness of the respective intraocular lens 7 to be folded, thereby to ensure that, even when dealing with lenses of different thicknesses, the hold-down member 1 bears against the lens 7 to be folded practically without applying a force thereto.

It will be appreciated that the above-described method and apparatus have been set forth solely by way of example and illustration of the present invention and that various other modifications and alterations may be made therein without departing from the scope of the invention.

What is claimed is:

1. Apparatus for folding a resilient intraocular lens comprising a support surface for supporting the lens to be folded, a hold-down member movable towards said support surface to hold the lens thereon, first and second feed pressing members which have faces facing towards each other from opposite sides of the support surface and which are synchronously movable in mutually opposite relationship to a position of being brought together at which said faces thereof which are in contact with the lens on the support surface fold the lens to reproduce in a slightly reduced fashion the internal contour of a tube member of an implantation instrument for subsequent implantation of the lens, and an insertion press member movable to insert the folded lens into the interior of said implantation instrument tube member.

2. Apparatus as set forth in claim 1 and further including an abutment means for defining the lens holding position of the hold-down member, in which position the hold-down member contacts the lens practically without applying a force thereto.

3. Apparatus as set forth in claim 1 wherein said hold-down member is of an elongate cross-section in the direction of movement of said insertion member.

4. Apparatus as set forth in claim 1 wherein the direction of movement of the insertion member is at least substantially perpendicular to the direction of movement of the pressing members.

5. A method of folding a resilient intraocular lens and inserting same into a tube member of a lens implantation instrument, comprising: holding the lens on a support surface with a hold-down member movable towards said support surface to hold the lens thereon in an at least substantially planar condition; applying forces to said lens at respective oppositely disposed sides thereof, thereby to cause said sides to move towards each other by bending said lens out of said planar condition, the lens being folded to a configuration which at least substantially reproduces the internal configuration of said implantation instrument tube member while being slightly smaller than said internal configuration of said tube member; releasing the folded lens from the support surface; and moving the lens in the folded condition into the interior of said tube member.

* * * * *